United States Patent
Bondos et al.

(10) Patent No.: US 12,344,638 B2
(45) Date of Patent: Jul. 1, 2025

(54) FUNCTIONALIZED UBX PROTEIN MATERIALS FOR ENHANCED PURIFICATION OF ANTIBODIES

(71) Applicant: BONDWELL TECHNOLOGIES INC., College Station, TX (US)

(72) Inventors: Sarah E. Bondos, College Station, TX (US); David W. Howell, College Station, TX (US)

(73) Assignee: BONDWELL TECHNOLOGIES LP, College Station, TX (US)

( * ) Notice: Subject to any disclaimer, the term of this patent is extended or adjusted under 35 U.S.C. 154(b) by 634 days.

(21) Appl. No.: 17/600,960

(22) PCT Filed: Apr. 2, 2020

(86) PCT No.: PCT/US2020/026412
§ 371 (c)(1),
(2) Date: Oct. 1, 2021

(87) PCT Pub. No.: WO2020/206138
PCT Pub. Date: Oct. 8, 2020

(65) Prior Publication Data
US 2022/0251147 A1     Aug. 11, 2022

Related U.S. Application Data

(60) Provisional application No. 62/828,142, filed on Apr. 2, 2019.

(51) Int. Cl.
*C07K 14/31* (2006.01)
*C07K 1/22* (2006.01)
*C07K 14/435* (2006.01)

(52) U.S. Cl.
CPC .............. *C07K 14/31* (2013.01); *C07K 1/22* (2013.01); *C07K 14/43563* (2013.01)

(58) Field of Classification Search
CPC ........................... C07K 1/22; C07K 2319/705
See application file for complete search history.

(56) References Cited

U.S. PATENT DOCUMENTS

| | | |
|---|---|---|
| 2007/0248536 A1 | 10/2007 | Fiedler |
| 2010/0063256 A1 | 3/2010 | Spector |
| 2010/0143436 A1* | 6/2010 | Bondos .................. A61P 17/02 424/443 |
| 2013/0245224 A1 | 9/2013 | Bjorkman |
| 2015/0087046 A1* | 3/2015 | Hedhammar .......... C07K 14/36 435/325 |
| 2018/0222949 A1* | 8/2018 | Bondos .................... A61K 9/70 |

FOREIGN PATENT DOCUMENTS

| | | | |
|---|---|---|---|
| JP | 2016121152 A | 7/2016 | |
| WO | 2010057032 | 5/2010 | |
| WO | WO-2017200461 A1 * | 11/2017 | ............... C07K 1/22 |
| WO | 2018151743 | 8/2018 | |
| WO | WO-2018151743 A1 * | 8/2018 | ......... B01D 15/3804 |

OTHER PUBLICATIONS

International Application No. PCT/US2020/026412, International Preliminary Report on Patentability, Mailed On Oct. 14, 2021, 8 pages.
International Application No. PCT/US2020/026412, International Search Report and Written Opinion, Mailed On Jul. 9, 2020, 13 pages.
Tsai et al., "The Effect of Protein Fusions on the Production and Mechanical Properties of Protein-Based Materials", Advanced Functional Materials, vol. 25, No. 9, Mar. 1, 2015, pp. 1442-1450.
Tsai, "Ubx as a Novel Protein-Based Material: Structural Insights, Functionalization via Gene Fusion and Biomedical Applications", XP55707829, Available Online at: https://oaktrust.library.tamu.edu/bitstream/handle/1969.1/187418/TSAI%20-DISSERTATION%20-2016.pdf?sequence=1&isAllowed=y, May 2016, 179 pages.
Chinese Application No. CN202080039393.0, Office Action mailed Sep. 28, 2023, 10 pages.
European Patent Application No. EP20722745.5, Office Action mailed May 6, 2024, 4 pages.
Japanese Patent Application No. JP2021-560489, Office Action mailed Apr. 26, 2024, 14 pages.
Singapore Application No. 11202110947R, Further Written Opinion mailed May 24, 2024, 8 pages.
Singapore Application No. 11202110947R, "Written Opinion," Mailed on Jul. 11, 2023, 8 pages.

\* cited by examiner

*Primary Examiner* — Anand U Desai
(74) *Attorney, Agent, or Firm* — Kilpatrick Townsend & Stockton LLP

(57) ABSTRACT

Provided herein are methods and compositions for purifying antibodies. Purification is achieved by increasing the binding capacity of protein A chromatography by covalent attachment of a protein A domain (E, D, A, B, C), or domain Z, or a functional variant thereof, to *Drosophila melanogaster* transcription factor Ultrabithorax (Ubx) materials. The compositions include fusion proteins containing *Drosophila melanogaster* transcription factor Ultrabithorax (Ubx) or a fragment thereof and an immunoglobulin binding protein. In some embodiments, the immunoglobulin binding protein is a protein A domain, a protein Z domain or a fragment thereof.

9 Claims, 4 Drawing Sheets
Specification includes a Sequence Listing.

Run 1

Run 2

SEQUENCE LISTING

<160> NUMBER OF SEQ ID NOS: 25

<210> SEQ ID NO 1
<211> LENGTH: 60
<212> TYPE: PRT

```
<213> ORGANISM: Artificial sequence
<220> FEATURE:
<223> OTHER INFORMATION: Synthetic construct

<400> SEQUENCE: 1

His Met Val Asp Asn Lys Phe Asn Lys Glu Gln Gln Asn Ala Phe Tyr
 1               5                  10                  15

Glu Ile Leu His Leu Pro Asn Leu Asn Glu Glu Gln Arg Asn Ala Phe
                20                  25                  30

Ile Gln Ser Leu Lys Asp Asp Pro Ser Gln Ser Ala Asn Leu Leu Ala
            35                  40                  45

Glu Ala Lys Lys Leu Asn Asp Ala Gln Ala Pro Lys
    50                  55                  60

<210> SEQ ID NO 2
<211> LENGTH: 56
<212> TYPE: PRT
<213> ORGANISM: Artificial sequence
<220> FEATURE:
<223> OTHER INFORMATION: Synthetic construct

<400> SEQUENCE: 2

Ala Gln His Asp Glu Ala Gln Gln Asn Ala Phe Tyr Gln Val Leu Asn
 1               5                  10                  15

Met Pro Asn Leu Asn Ala Asp Gln Arg Asn Gly Phe Ile Gln Ser Leu
                20                  25                  30

Lys Asp Asp Pro Ser Gln Ser Ala Asn Val Leu Gly Glu Ala Gln Lys
            35                  40                  45

Leu Asn Asp Ser Gln Ala Pro Lys
    50                  55

<210> SEQ ID NO 3
<211> LENGTH: 58
<212> TYPE: PRT
<213> ORGANISM: Artificial sequence
<220> FEATURE:
<223> OTHER INFORMATION: Synthetic construct

<400> SEQUENCE: 3

Ala Asp Asn Asn Phe Asn Lys Glu Gln Gln Asn Ala Phe Tyr Glu Ile
 1               5                  10                  15

Leu Asn Met Pro Asn Leu Asn Glu Glu Gln Arg Asn Gly Phe Ile Gln
                20                  25                  30

Ser Leu Lys Asp Asp Pro Ser Gln Ser Ala Asn Leu Leu Ser Glu Ala
            35                  40                  45

Lys Lys Leu Asn Glu Ser Gln Ala Pro Lys
    50                  55

<210> SEQ ID NO 4
<211> LENGTH: 58
<212> TYPE: PRT
<213> ORGANISM: Artificial sequence
<220> FEATURE:
<223> OTHER INFORMATION: Synthetic construct

<400> SEQUENCE: 4

Ala Asp Asn Lys Phe Asn Lys Glu Gln Gln Asn Ala Phe Tyr Glu Ile
 1               5                  10                  15

Leu His Leu Pro Asn Leu Asn Glu Glu Gln Arg Asn Gly Phe Ile Gln
                20                  25                  30

Ser Leu Lys Asp Asp Pro Ser Gln Ser Ala Asn Leu Leu Ala Glu Ala
```

```
                35                  40                  45
Lys Lys Leu Asn Asp Ala Gln Ala Pro Lys
    50                  55

<210> SEQ ID NO 5
<211> LENGTH: 58
<212> TYPE: PRT
<213> ORGANISM: Artificial sequence
<220> FEATURE:
<223> OTHER INFORMATION: synthetic construct

<400> SEQUENCE: 5

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 6
<211> LENGTH: 55
<212> TYPE: PRT
<213> ORGANISM: Artificial sequence
<220> FEATURE:
<223> OTHER INFORMATION: Synthetic construct

<400> SEQUENCE: 6

Thr Tyr Lys Leu Ile Leu Asn Gly Lys Thr Leu Lys Gly Glu Thr Thr
1               5                   10                  15

Thr Glu Ala Val Asp Ala Ala Thr Ala Glu Lys Val Phe Lys Gln Tyr
            20                  25                  30

Ala Asn Asp Asn Gly Val Asp Gly Glu Trp Thr Tyr Asp Asp Ala Thr
        35                  40                  45

Lys Thr Phe Thr Val Thr Glu
    50                  55

<210> SEQ ID NO 7
<211> LENGTH: 55
<212> TYPE: PRT
<213> ORGANISM: Artificial sequence
<220> FEATURE:
<223> OTHER INFORMATION: Synthetic construct

<400> SEQUENCE: 7

Thr Tyr Lys Leu Val Ile Asn Gly Lys Thr Leu Lys Gly Glu Thr Thr
1               5                   10                  15

Thr Glu Ala Val Asp Ala Ala Thr Ala Glu Lys Val Phe Lys Gln Tyr
            20                  25                  30

Ala Asn Asp Asn Gly Val Asp Gly Glu Trp Thr Tyr Asp Asp Ala Thr
        35                  40                  45

Lys Thr Phe Thr Val Thr Glu
    50                  55

<210> SEQ ID NO 8
<211> LENGTH: 55
<212> TYPE: PRT
<213> ORGANISM: Artificial sequence
<220> FEATURE:
<223> OTHER INFORMATION: Synthetic construct
```

<400> SEQUENCE: 8

Thr Tyr Lys Leu Val Ile Asn Gly Lys Thr Leu Lys Gly Glu Thr Thr
1               5                   10                  15

Thr Lys Ala Val Asp Ala Glu Thr Ala Glu Lys Ala Phe Lys Gln Tyr
            20                  25                  30

Ala Asn Asp Asn Gly Val Asp Gly Val Trp Thr Tyr Asp Ala Thr
        35                  40                  45

Lys Thr Phe Thr Val Thr Glu
        50                  55

<210> SEQ ID NO 9
<211> LENGTH: 58
<212> TYPE: PRT
<213> ORGANISM: Artificial sequence
<220> FEATURE:
<223> OTHER INFORMATION: Synthetic construct

<400> SEQUENCE: 9

Val Thr Ile Lys Ala Asn Leu Ile Phe Ala Asp Gly Ser Thr Gln Asn
1               5                   10                  15

Ala Glu Phe Lys Gly Thr Phe Ala Lys Ala Val Ser Asp Ala Tyr Ala
            20                  25                  30

Tyr Ala Asp Ala Leu Lys Lys Asp Asn Gly Glu Tyr Thr Val Asp Val
        35                  40                  45

Ala Asp Lys Gly Leu Thr Leu Asn Ile Lys
        50                  55

<210> SEQ ID NO 10
<211> LENGTH: 59
<212> TYPE: PRT
<213> ORGANISM: Artificial sequence
<220> FEATURE:
<223> OTHER INFORMATION: Synthetic construct

<400> SEQUENCE: 10

Val Thr Ile Lys Val Asn Leu Ile Phe Ala Asp Gly Lys Thr Gln Thr
1               5                   10                  15

Ala Glu Phe Lys Gly Thr Phe Glu Glu Ala Thr Ala Lys Ala Tyr Ala
            20                  25                  30

Tyr Ala Asp Leu Leu Ala Lys Glu Asn Gly Glu Tyr Thr Ala Asp Leu
        35                  40                  45

Glu Asp Gly Gly Asn Thr Ile Asn Ile Lys Phe
        50                  55

<210> SEQ ID NO 11
<211> LENGTH: 61
<212> TYPE: PRT
<213> ORGANISM: Artificial sequence
<220> FEATURE:
<223> OTHER INFORMATION: Synthetic construct

<400> SEQUENCE: 11

Val Thr Ile Lys Val Asn Leu Ile Phe Ala Asp Gly Lys Ile Gln Thr
1               5                   10                  15

Ala Glu Phe Lys Gly Thr Phe Glu Glu Ala Thr Ala Lys Ala Tyr Ala
            20                  25                  30

Tyr Ala Asn Leu Leu Ala Lys Glu Asn Gly Glu Tyr Thr Ala Asp Leu
        35                  40                  45

Glu Asp Gly Gly Asn Thr Ile Asn Ile Lys Phe Ala Gly
        50                  55                  60

```
<210> SEQ ID NO 12
<211> LENGTH: 61
<212> TYPE: PRT
<213> ORGANISM: Artificial sequence
<220> FEATURE:
<223> OTHER INFORMATION: Synthetic construct

<400> SEQUENCE: 12

Val Thr Ile Lys Val Asn Leu Ile Phe Ala Asp Gly Lys Thr Gln Thr
1               5                   10                  15

Ala Glu Phe Lys Gly Thr Phe Glu Glu Ala Thr Ala Glu Ala Tyr Arg
                20                  25                  30

Tyr Ala Asp Leu Leu Ala Lys Val Asn Gly Glu Tyr Thr Ala Asp Leu
            35                  40                  45

Glu Asp Gly Gly Tyr Thr Ile Asn Ile Lys Phe Ala Gly
        50                  55                  60

<210> SEQ ID NO 13
<211> LENGTH: 56
<212> TYPE: PRT
<213> ORGANISM: Artificial sequence
<220> FEATURE:
<223> OTHER INFORMATION: Synthetic construct

<400> SEQUENCE: 13

Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
                20                  25                  30

Lys Asp Asp Pro Ser Gln Ser Ala Asn Val Leu Gly Glu Ala Gln Lys
            35                  40                  45

Leu Asn Asp Ser Gln Ala Pro Lys
        50                  55

<210> SEQ ID NO 14
<211> LENGTH: 61
<212> TYPE: PRT
<213> ORGANISM: Artificial sequence
<220> FEATURE:
<223> OTHER INFORMATION: Synthetic construct

<400> SEQUENCE: 14

Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Ala Gln Arg Asn Gly
                20                  25                  30

Phe Ile Gln Ser Leu Lys Asp Asp Pro Ser Gln Ser Thr Asn Val Leu
            35                  40                  45

Gly Glu Ala Lys Lys Leu Asn Glu Ser Gln Ala Pro Lys
        50                  55                  60

<210> SEQ ID NO 15
<211> LENGTH: 58
<212> TYPE: PRT
<213> ORGANISM: Artificial sequence
<220> FEATURE:
<223> OTHER INFORMATION: Synthetic construct

<400> SEQUENCE: 15

Ala Asp Asn Asn Phe Asn Lys Glu Gln Gln Asn Ala Phe Tyr Glu Ile
1               5                   10                  15
```

-continued

Leu Asn Met Pro Asn Leu Asn Glu Glu Gln Arg Asn Gly Phe Ile Gln
                20                  25                  30

Ser Leu Lys Asp Asp Pro Ser Gln Ser Ala Asn Leu Leu Ser Glu Ala
            35                  40                  45

Lys Lys Leu Asn Glu Ser Gln Ala Pro Lys
        50                  55

<210> SEQ ID NO 16
<211> LENGTH: 58
<212> TYPE: PRT
<213> ORGANISM: Artificial sequence
<220> FEATURE:
<223> OTHER INFORMATION: Synthetic construct

<400> SEQUENCE: 16

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 17
<211> LENGTH: 58
<212> TYPE: PRT
<213> ORGANISM: Artificial sequence
<220> FEATURE:
<223> OTHER INFORMATION: Synthetic construct

<400> SEQUENCE: 17

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
                20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro Lys
        50                  55

<210> SEQ ID NO 18
<211> LENGTH: 55
<212> TYPE: PRT
<213> ORGANISM: Artificial sequence
<220> FEATURE:
<223> OTHER INFORMATION: Synthetic construct

<400> SEQUENCE: 18

Thr Tyr Lys Leu Ile Leu Asn Gly Lys Thr Leu Lys Gly Glu Thr Thr
1               5                   10                  15

Thr Glu Ala Val Asp Ala Ala Thr Ala Glu Lys Val Phe Lys Gln Tyr
                20                  25                  30

Ala Asn Asp Asn Gly Val Asp Gly Glu Trp Thr Tyr Asp Asp Ala Thr
            35                  40                  45

Lys Thr Phe Thr Val Thr Glu
        50                  55

<210> SEQ ID NO 19
<211> LENGTH: 55

<212> TYPE: PRT
<213> ORGANISM: Artificial sequence
<220> FEATURE:
<223> OTHER INFORMATION: Synthetic construct

<400> SEQUENCE: 19

```
Thr Tyr Lys Leu Val Ile Asn Gly Lys Thr Leu Lys Gly Glu Thr Thr
1               5                   10                  15

Thr Lys Ala Val Asp Ala Glu Thr Ala Glu Lys Ala Phe Lys Gln Tyr
            20                  25                  30

Ala Asn Asp Asn Gly Val Asp Gly Val Trp Thr Tyr Asp Asp Ala Thr
        35                  40                  45

Lys Thr Phe Thr Val Thr Glu
    50                  55
```

<210> SEQ ID NO 20
<211> LENGTH: 61
<212> TYPE: PRT
<213> ORGANISM: Artificial sequence
<220> FEATURE:
<223> OTHER INFORMATION: Synthetic construct

<400> SEQUENCE: 20

```
Leu Arg Arg Arg Gly Arg Gln Thr Tyr Thr Arg Tyr Gln Thr Leu Glu
1               5                   10                  15

Leu Glu Lys Glu Phe His Thr Asn His Tyr Leu Thr Arg Arg Arg Arg
            20                  25                  30

Ile Glu Met Ala His Ala Leu Cys Leu Thr Glu Arg Gln Ile Lys Ile
        35                  40                  45

Trp Phe Gln Asn Arg Arg Met Lys Leu Lys Lys Glu Ile
    50                  55                  60
```

<210> SEQ ID NO 21
<211> LENGTH: 8
<212> TYPE: PRT
<213> ORGANISM: Artificial sequence
<220> FEATURE:
<223> OTHER INFORMATION: Synthetic construct

<400> SEQUENCE: 21

```
Met Asn Ser Tyr Phe Glu Gln Ala
1               5
```

<210> SEQ ID NO 22
<211> LENGTH: 19
<212> TYPE: PRT
<213> ORGANISM: Artificial sequence
<220> FEATURE:
<223> OTHER INFORMATION: Synthetic construct

<400> SEQUENCE: 22

```
Val Arg Pro Ser Ala Cys Thr Pro Asp Ser Arg Val Gly Gly Tyr Leu
1               5                   10                  15

Asp Thr Ser
```

<210> SEQ ID NO 23
<211> LENGTH: 8
<212> TYPE: PRT
<213> ORGANISM: Artificial sequence
<220> FEATURE:
<223> OTHER INFORMATION: Synthetic construct

<400> SEQUENCE: 23

```
Phe Tyr Pro Trp Met Ala Ile Ala
1               5

<210> SEQ ID NO 24
<211> LENGTH: 4
<212> TYPE: PRT
<213> ORGANISM: Artificial sequence
<220> FEATURE:
<223> OTHER INFORMATION: Synthetic construct

<400> SEQUENCE: 24

Ser Gly Ser Gly
1

<210> SEQ ID NO 25
<211> LENGTH: 4
<212> TYPE: PRT
<213> ORGANISM: Artificial sequence
<220> FEATURE:
<223> OTHER INFORMATION: Synthetic construct

<400> SEQUENCE: 25

Gly Ser Gly Ser
1
```

FUNCTIONALIZED UBX PROTEIN MATERIALS FOR ENHANCED PURIFICATION OF ANTIBODIES

PRIOR RELATED APPLICATION

This application is a U.S. National Phase under 35 U.S.C. § 371 of International Patent Application No. PCT/US2020/026412, filed Apr. 2, 2021, which claims the benefit of U.S. Provisional Application No. 62/828,142 filed on Apr. 2, 2019 which is hereby incorporated by reference in its entirety.

BACKGROUND

Antibody-based therapeutics effectively target specific molecules or cells with few adverse effects. However, antibody therapies are expensive, and more antibody therapies are in clinical trials than can be manufactured using existing facilities. Therefore, the industrial refinement of antibody purification methods is essential to reduce manufacturing cost and increase efficiency. There are many established methods by which antibodies may be isolated and purified, such as class-specific affinity chromatography, anion exchange chromatography, or antigen-specific affinity chromatography. The most common affinity ligand is protein A, a 41 kD cell wall protein from *Staphylococcus aureus* that binds the Fc region of human immunoglobulin G (IgG). Additional affinity ligands are Protein G (65 kD, IgG binding protein of group G streptococci), Protein L (76 Kd binding protein of *Peptostreptococcus magnus*), and Protein A/G (a recombinant fusion protein that combines IgG binding domains of both Protein A and Protein G, which are functional variants of *Staphylococcus aureus* Protein A. Protein A chromatography has been widely recognized as the gold standard for antibody purification due to its high selectivity (90% purity) and capacity (60 mg of antibody per 1 ml of resin).

In U.S. Pat. No. 6,127,526, the traditional technique for isolating and purifying proteins via Protein A affinity chromatography is described. The purification process entails: (i.) the immobilization of a Protein A domain (E, D, A, B, C), or a functional variant thereof on a solid phase; (ii.) eliminating contaminants through the washing of solid phase materials with a hydrophobic electrolyte solution; and (iii.) isolation of desired protein from the solid phase. The type of solid support can dramatically affect the antibody purification process. Commonly utilized solid matrices may consist of materials like silica or agarose; however, the method of attaching Staphylococcal protein A (SpA) to the solid support is also important. While Protein A chromatography is the dominant method for antibody purification, given the significant cost associated with Protein A chromatography and current limitations related to throughput, scale-up and ligand leeching, alternative purification methods are necessary.

SUMMARY

The present disclosure is directed to a composition and methods for increasing the binding capacity of protein A chromatography by covalent attachment of a protein A domain (E, D, A, B, C) or a synthetic protein Z, for example, a synthetic Z domain, to *Drosophila melanogaster* transcription factor Ultrabithorax (Ubx) materials. The inventors have discovered that Ubx materials incorporate about 1,000-fold greater SpA protein per gram of material than commercial chromatography resins crosslinked to the same SpA protein. The compositions provided herein include fusion proteins containing *Drosophila melanogaster* transcription factor Ultrabithorax (Ubx) or a fragment thereof and an immunoglobulin binding protein. In some embodiments, the immunoglobulin binding protein is a protein A domain, a protein Z domain or a fragment thereof.

An affinity chromatography matrix comprising from about 2 to about 18 immunoglobulin binding domains, for example, SpA or Z domain repeats, is also provided. By covalently attaching multiple immunoglobulin binding domains, for example, from about 2 to about 18 SpA or Z domain repeats, to a Ubx protein or a fragment thereof, binding capacity can be increased. A common problem associated with other SpA applications is that the chemical fixation of SpA domains to solid phase matrices is susceptible to degradation leading to leeching of protein A. See, for example, US Patent Application Publication No. 20050038231. The compositions and methods provided herein allow for increased immunoglobulin purity by preventing SpA contamination through ligand leaching. Covalent attachment of an SpA domain repeat(s), a Z domain(s) or a fragment thereof to Ubx materials prevents ligand leaching or disassociation from the matrix. Thus, the invention provides an antibody affinity separation matrix with increased capacity that allows for isolation of immunoglobulins with increased purity. Methods of using any of the affinity separation matrices provided herein to isolate or purify antibodies or immunoglobulin-containing proteins are also provided.

DEFINITIONS

Figure 1:
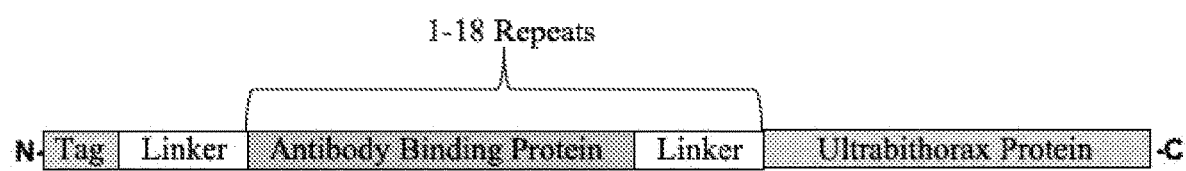
FIG. 1 is a schematic of a Z domain or up to 18 Z domains fused to Ubx via a short linker (s). A tag for purification is attached to the entire fusion protein via a similar linker.

Provided herein are an antibody affinity protein immobilized to a Ubx material scaffold. This is accomplished via a fusion protein composed of an antibody binding domain and a material forming Ubx protein. Uses of Ubx materials for the purification of immunoglobulins are also provided. The invention is based on the discovery that affinity purification binding capacity can be significantly improved because Ubx materials incorporate 1,000 times more SpA protein per gram of material than commercial chromatography resins crosslinked to the same SpA protein. Additionally, covalent binding of antibody affinity domains to Ubx materials prevents leaching of the ligand from the support thereby improving product purity.

The terms "polypeptide," "peptide," and "protein" are used interchangeably herein to refer to a polymer of amino acid residues. The terms encompass amino acid chains of any length, including full-length proteins, wherein the amino acid residues are linked by covalent peptide bonds. The definition also includes fragments and variants of any polypeptide described herein. The protein may be an antibody. The protein may be produced by host cells.

The terms "antibody affinity domain," and "immunoglobulin binding protein" are used interchangeably and can be, for example, a protein A domain (for example, E, D, A, B, C, or Z), or a protein G domain, a protein L domain, a protein A/G domain, or a functional variant thereof. In some embodiments, the antibody affinity domain can be a Staphylococcal protein A (SpA) domain. In some embodiments, the antibody affinity domain comprises, consists essentially of, or consists of a Z domain, for example, a synthetic Z domain, such as, SEQ ID NO: 1 (HMVDNKFNKEQQNAFYEILHLPNLNEEQR-NAFIQSLKDDPSQSANLLAEAKKLNDAQAPK), or a fragment thereof. In some embodiments, the affinity domain comprises, consists essentially of, or consists of an SpA domain E (AQHDEAQQNAFYQVLNMPNLNADQRNG-FIQSLKDDPSQSANVLGEAQKLNDSQAPK (SEQ ID NO: 2)), an SpA domain A (ADNNFNKEQQNAFYEILNMPNLNEEQRNG-FIQSLKDDPSQSANLLSEAKKLNESQAPK (SEQ ID NO: 3)), an SpA domain B (ADNKFNKEQQNAFYEILHLPNLNEEQRNG-FIQSLKDDPSQSANLLAEAKKLNDAQAPK (SEQ ID NO: 4)), an SpA domain C (ADNKFNKEQQNAFYEILHLPNLTEEQRNG-FIQSLKDDPSVSKEILAEAKKLNDAQAPK (SEQ ID NO: 5)), an SpA domain D (SEQ ID NO: 14), a protein G domain (for example, a protein G C1 domain (TYKLILNGKTLKGETTTEAVDAATAEKVFKQY-ANDNGVDGEWTYDDATKTFTVTE) (SEQ ID NO: 6)); a protein G C2 domain (TYKLV-INGKTLKGETTTEAVDAATAEKVFKQY-ANDNGVDGEWTYDDATKTFTVTE) (SEQ ID NO: 7); or a protein G C3 domain (TYKLVINGKTLKGETTTKAV-DAETAEKAFKQYANDNGVDGVWTYDDATKTFTVTE (SEQ ID NO: 8)), a protein L domain (for example, B1: (VTIKANLIFADGSTQNAEFKGTFAKAVSDAYAY-ADALKKDNGEYTVDVADKGLTLNIKFAG) (SEQ ID NO: 9)); B2: (VTIKVNLIFADGKTQTAEFKGTFEEATA-KAYAYADLLAKENGEYTADLEDGGNTINIKFAG) (SEQ ID NO:10)); B3: (VTIKVNLIFADGKIQTAEFKGT-FEEATAKAYAYANLLAKENGEYTADLEDGGN-TINIKFAG) (SEQ ID NO: 11)); or B4: (VTIKVNLI-FADGKTQTAEFKGTFEEATAEAYRYADLLAKVNGE-YTADLEDGGYTINIKFAG) (SEQ ID NO: 12); a protein A/G domain (for example, (AQHDEA-QQNAFYQVLNMPNLNADQRNGFIQSLKDDP-SQSANVLGEAQKLNDSQAPK) (SEQ ID NO: 13)); (ADAQQNNFNKDQQSAFYEILNMPNLNEAQRNG-FIQSLKDDPSQSTNVLGEAKKLNESQAPK) (SEQ ID NO: 14)); (ADNNFNKEQQNAFYEILNMPNLNE-EQRNGFIQSLKDDPSQSANLLSEAKKLNESQAPK) (SEQ ID NO: 15); (ADNKFNKEQQNAFYEILHLPNL-NEEQRNGFIQSLKDDPSQSANLLAEAKKLN-DAQAPK) (SEQ ID NO: 16)); (ADNKFNKEQQNAFYEILHLPNLTEEQRNG-FIQSLKDDPSVSKEILAEAKKLNDAQAPK (SEQ ID NO: 17)); (TYKLILNGKTLKGETTTEAVDAA-TAEKVFKQYANDNGVDGEWTYDDATKTFTVTE) (SEQ ID NO: 18)) or (TYKLVINGKTLKGETTTKAV-DAETAEKAFKQYANDNGVDGVWTYDD-ATKTFTVTE) (SEQ ID NO: 19)), or a fragment thereof. Optionally, any fragment of an immunoglobulin binding protein described herein can be a binding fragment.

In some embodiments, one or more antibody affinity domains are present in any of the fusion proteins described herein. Optionally, an affinity domain comprises an amino acid sequence comprising, consisting essentially of, or consisting of one or more sequences selected from the group consisting of SEQ ID NO: 1 through SEQ ID NO: 19, or a functional fragment thereof.

The terms "solid phase", "support", "scaffold", and "matrices" are used herein interchangeably, and refer to the solid material that provides a physical structure to immobilize an antibody affinity domain.

The term "antibody" as used herein refers to an immunoglobulin (Ig) molecule, an antigen binding fragment thereof or a binding derivative thereof. An antigen binding fragment of an antibody contains an antigen binding site that specifically binds an antigen. The antibodies (Abs) may be monoclonal antibodies, polyclonal antibodies or multispecific antibodies (e.g., bispecific antibodies). Examples of antibodies include immunoglobulin (Ig) types IgG, IgD, IgE, IgA and IgM. The antibodies may be native antibodies or recombinant antibodies. The antibodies may be produced by host cells.

The term "fusion protein" as used herein refers to a protein containing two or more polypeptides that are derived from different proteins but produced as a single polypeptide from a polynucleotide including a nucleotide sequence encoding both proteins and, in some embodiments, a linking sequence, under control of a single promoter. The two or more polypeptides in the fusion proteins described herein are conjugated or linked, optionally, via a linker.

The term "nucleic acid" or "nucleotide" refers to deoxyribonucleic acids (DNA) or ribonucleic acids (RNA) and polymers thereof in either single- or double-stranded form. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated.

A "promoter" is defined as one or more a nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

A nucleic acid is "operably linked" when it is placed into a functional relationship with another nucleic acid sequence.

For example, a promoter or enhancer is operably linked to a coding sequence if it affects the transcription of the sequence; or a ribosome binding site is operably linked to a coding sequence if it is positioned so as to facilitate translation.

The term "Ubx material" or "Ubx materials" refers to the biomaterial made from the self-assembly of the *Drosophila melanogaster* transcription factor Ultrabithorax (US2010/0143436) or any of the improved synthetic versions of Ultrabithorax described in US 20180222949A1. In some examples, the Ubx material contains two or more self-assembled Ubx protein molecules. In any of the Ubx materials described herein, the Ubx protein can include an amino acid sequence selected from the group consisting of the amino acid sequence set forth under Gen Bank Accession No. AAN13717, Gen Bank Accession No. AAN13718, Gen Bank Accession No. AAN13719, Gen Bank Accession No. AAF55355, Gen Bank Accession No. AAF55356, and Gen Bank Accession No. AAS65158, or a fragment thereof. For purposes of comparison to other chromatography supports, 1 mL of Ubx material means the equivalent mass of Ubx material to 1 mL of settled agarose based resin.

In some embodiments, a full-length Ubx protein is used to create a fusion protein. See, for example, Uniprot No. P83949. In other embodiments, the Ubx protein that is used to produce a Ubx fusion protein is a fragment of a Ubx protein comprising a Ubx homeodomain, for example, a Ubx protein fragment comprising or containing SEQ ID NO: (LRRRGRQTYTRYQTLELEKEFHTNHYLTRRRRI-EMAHALCLTERQIKIWFQNRRMKLKKEI). In other embodiments, the Ubx fusion protein comprises a Ubx protein fragment containing SEQ ID NO: 20 and SEQ ID NO:21 (MNSYFEQA). In other embodiments, the Ubx fusion protein includes a Ubx protein fragment containing SEQ ID NO:22 (VRPSACTPDSRVGGYLDTS) and/or SEQ ID NO: 23 (FYPWMAIA). It is understood that the term "Ubx protein" means a full-length Ubx protein or a fragment thereof.

The term "functional material" refers to a Ubx biomaterial made from a fusion protein containing an immunoglobulin binding protein and a Ubx protein or a fragment thereof. In some embodiments, the Ubx biomaterial comprises two or more self-assembled fusion proteins comprising an immunoglobulin binding protein and a Ubx protein.

DETAILED DESCRIPTION

Compositions

The present invention relates to a composition containing a biomaterial for purification of antibodies. In some embodiments, the biomaterial includes a Ubx protein or a fragment thereof. The biomaterials provided herein have a functional property that is imparted through fusion of an antibody or immunoglobulin binding protein to a Ubx protein or a fragment thereof. The immunoglobulin-binding protein can be any protein with a native immunoglobulin-binding capability, such as Staphylococcal protein A (SpA), Streptococcal protein G (SpG), *Peptostreptococcus* protein L, Protein A/G, or recombinant proteins containing IgG-binding domains of these proteins. For a review of such proteins, see, for example, Kronvall and Jonsson (Receptins: a novel term for an expanding spectrum of natural and engineered microbial proteins with binding properties for mammalian proteins, *J. Mol. Recognit.* 1999 January-February; 12(1):38-44). The immunoglobulin-binding protein can contain one of more of the E, D, A, B and C domains of SpA. In some embodiments, the immunoglobulin-binding protein contains domain B of protein A or an engineered, synthetic protein Z domain. In some embodiments, multimeric ligands containing two or more, such as 2-18, copies of the same monomeric domain from domain E, D, A, B, or C of protein A, or domain Z (FIG. 1). In other embodiments, multimeric ligands containing two or more, such as 2-18, different monomeric domains selected from domain E, D, A, B, and C of protein A, or domain Z can be used. Functional variants of domain E, D, A, B or C of protein A or domain Z can be used in any of the embodiments described herein.

In some embodiments, the functional property of antibody binding is imparted through a fusion protein including an immunoglobulin, an antibody binding protein and a Ubx protein or a fragment thereof. The nucleic acid or gene encoding the functional fusion protein is cloned into a plasmid for expressing the protein, generally 3' to a DNA sequence encoding a peptide tag (for example, a histidine tag) to facilitate protein purification. Other tags known in the art, for example, a chemical moiety, such as, a fluorescent tag, can also be used. The fusion protein can be expressed in cells, for example, eukaryotic or prokaryotic cells. Cells comprising a nucleic acid sequence encoding any of the fusion proteins herein are also provided. Optionally, the nucleic acid sequence is in a vector. Optionally, the nucleic acid sequence is stably integrated into the genome of the cell. Expression of the fusion protein can be under the control of an appropriate promoter, for example, any constitutive or regulatable promoter known to those of skill in the art.

In some embodiments, a linker is placed at the 3' end of the nucleic acid sequence encoding the immunoglobulin binding protein. The length and sequence of this linker can vary. For example, the linker can be from about two to about twenty amino acids in length. In some embodiments, the linker contains alternating repeats of glycine and serine, for example, $(SGSG)_n$ (SEQ ID NO: 24) or $(GSGS)_n$ (SEq ID NO: 25), wherein n is an integer. When a linker is present, the nucleic acid encoding the Ubx protein or a fragment thereof is located at the 3' end of the linker followed by one or more stop codons, the only one(s) in the gene fusion. Expression of the fused gene in host cells produces the fused protein, which can be used to make functionalized materials. See, for example, U.S. Patent Publication No. 20180222949 for methods of making fusion proteins and functionalized materials.

Figure 2:
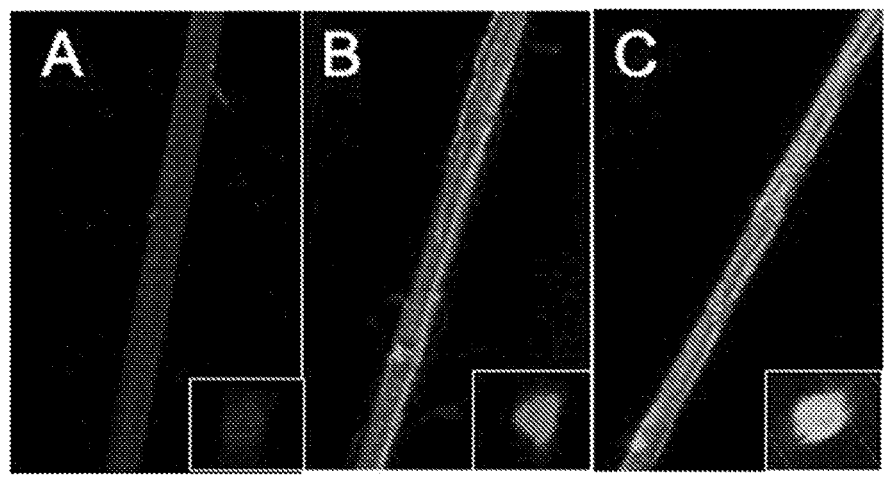
FIG. 2 A FITC labeled antibody fails to bind a fiber composed of plain Ubx (A) but does bind a Z-Ubx fiber (B), and a 18Z-Ubx fiber (C). Insets: cross sections demonstrate that antibody binds throughout the fibers.
Figure 3:
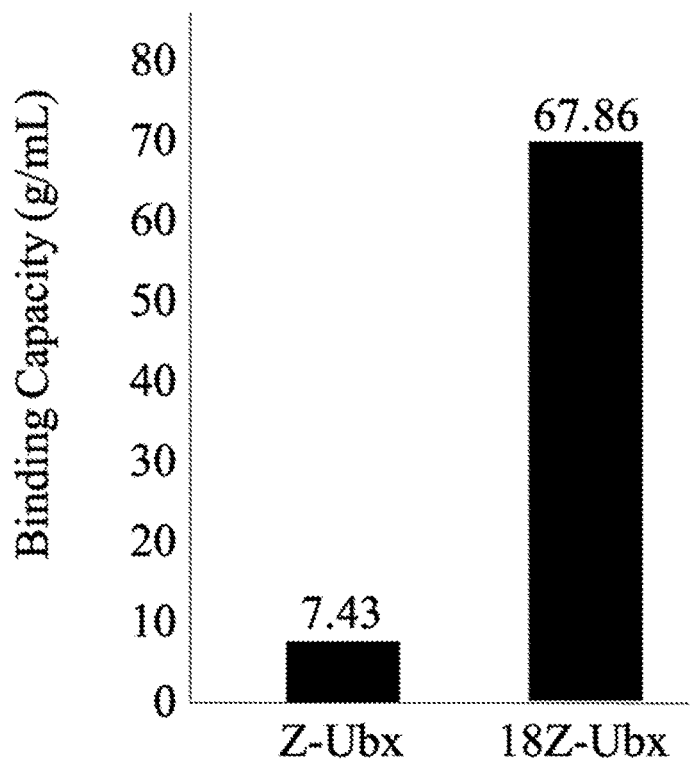
FIG. 3 is a graph showing quantification of static binding capacity for Z-Ubx and 18Z-Ubx.

Because Ubx materials incorporate 1,000-fold more protein per gram of material than commercial chromatography resins crosslinked to the same protein, by using the compositions and methods described herein, antibody can be bound to the functional biomaterial (FIG. 2) at a higher capacity than previously reported uses of antibody binding technologies (FIG. 3).

Provided herein is a fusion protein comprising at least one Ubx protein and an immunoglobulin binding protein. In some embodiments, the immunoglobulin binding protein comprises a single domain of staphylococcal Protein A (SpA), domain Z, or a functional variant thereof. In some embodiments, the domain of the staphylococcal Protein A (SpA) is the E, D, A, B or C domain. In some embodiments, the immunoglobulin binding protein contains two or more different monomeric domains of staphylococcal Protein A (SpA), domain Z, or a functional variant thereof. In some embodiments, the two or more different monomeric domains of the staphylococcal Protein A (SpA) are the E, D, A, B or C domains. In some embodiments, the immunoglobulin binding protein contains two or more monomeric domains of staphylococcal Protein A (SpA), domain Z, or a functional variant thereof, wherein the monomeric domains are the same. In some embodiments, the two or more different monomeric domains of the staphylococcal Protein A (SpA) are the E, D, A, B or C domains.

Also provided herein is a solid matrix comprising any of the fusion proteins described herein. In some embodiments, leaching of the immunoglobulin binding protein from the solid matrix is prevented or reduced. For example, leaching can be reduced by at least 55, 10%, 20%, 30%, 40%, 50%, 60%, 70%, 80%, 90% or 100%. In some embodiments, the binding capacity of 1 mL of material is greater than 1 g/mL.

In some embodiments, the fusion protein comprises a Ubx protein fragment comprising or containing SEQ ID NO: 20 (LRRRGRQTYTRYQTLELEKEFHTNHYLTRRRRI-EMAHALCLTERQIKIWFQNRRMKLKKEI). In other embodiments, the Ubx fusion protein is composed of a Ubx protein fragment containing SEQ ID NO: 20 and SEQ ID NO:21 (MNSYFEQA). In other embodiments, the Ubx fusion protein includes a Ubx protein fragment containing SEQ ID NO:22 (VRPSACTPDSRVGGYLDTS) and/or SEQ ID NO: 23 (FYPWMAIA). A fusion protein comprising an amino acid sequence having at least 60%, 65%, 70%, 75%, 80%, 85%, 90%, 91%, 92%, 93%, 94%, 95%, 96%, 97%, 98%, or 99% identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21. SEQ ID NO: 2 and SEQ ID NO: 23 are also provided. The term "identity," as used in the context of polynucleotide or polypeptide sequences, refers to a sequence that has at least 60% sequence identity to a reference sequence. Alternatively, percent identity can be any integer from 60% to 100%. Exemplary embodiments include at least: 60%, 65%, 70%, 75%, 80%, 85%, 90%, 91%, 92%, 93%, 94%, 95%, 96%, 97%, 98%, or 99%, as compared to a reference sequence using the programs described herein; preferably BLAST using standard parameters, as described below. One of skill will recognize that these values can be appropriately adjusted to determine corresponding identity of proteins encoded by two nucleotide sequences by taking into account codon degeneracy, amino acid similarity, reading frame positioning and the like.

For sequence comparison, typically one sequence acts as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85: 2444 (1988), by computerized implementations of these algorithms (e.g., BLAST), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977)*Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about 10, and most preferably less than about $10^{-20}$.

The amino acids in the polypeptides described herein can be any of the 20 naturally occurring amino acids, D-stereoisomers of the naturally occurring amino acids, non-naturally occurring or unnatural amino acids, and chemically modified amino acids. Unnatural amino acids (that is, those that are not naturally found in proteins) are also known in the art, as set forth in, for example, Zhang et al. "Protein engineering with unnatural amino acids," *Curr. Opin. Struct. Biol.* 23(4): 581-587 (2013); Xie et la. "Adding amino acids to the genetic repertoire," 9(6): 548-54 (2005)); and all references cited therein. B and 7 amino acids are known in the art and are also contemplated herein as unnatural amino acids. Any of the synthetic peptides described herein, for example synthetic domain Z can be derived or engineered from a domain of SpA, for example, domain E, D, A, B or C.

As used herein, a chemically modified amino acid refers to an amino acid whose side chain has been chemically modified. For example, a side chain can be modified to comprise a signaling moiety, such as a fluorophore or a radiolabel. A side chain can also be modified to comprise a new functional group, such as a thiol, carboxylic acid, or amino group. Post-translationally modified amino acids are also included in the definition of chemically modified amino acids.

Also contemplated are one or more conservative amino acid substitutions in any one of the polypeptides described herein. By way of example, conservative amino acid substitutions can be made in one or more of the amino acid residues, for example, in one or more lysine residues of any of the polypeptides provided herein. One of skill in the art would know that a conservative substitution is the replacement of one amino acid residue with another that is biologically and/or chemically similar. The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

By way of example, when an arginine to serine is mentioned, also contemplated is a conservative substitution for the serine (e.g., threonine). Nonconservative substitutions, for example, substituting a lysine with an asparagine, are also contemplated.

Methods

Also provided herein are methods for separating one or more immunoglobulin containing proteins from a liquid or solution. The methods include (a) contacting the liquid with a separation matrix containing a ligand(s), i.e., an immunoglobulin binding protein, immobilized to a support; (b) allowing the immunoglobulin containing proteins to adsorb to the matrix by interaction with the ligand(s); (c) washing the adsorbed immunoglobulin containing proteins; and (d) recovering the immunoglobulin containing proteins by contacting the matrix with an eluent which releases the proteins. The method provides increased binding capacity of the ligands to the immunoglobulin molecules by using a ligand, each of which includes one or more domains (i.e., monomers) of staphylococcal Protein A (SpA) (E, D, A, B, C or Z), or a functional variant thereof.

In the methods described herein, the ligand, i.e., the immunoglobulin binding protein, is immobilized onto a protein-based biomaterial, i.e., a Ubx material, by fusing the protein ligand to a Ubx protein or a fragment thereof. In the methods provided herein, the matrix is composed of Ubx materials as a solid support. In all embodiments, the biomaterial is made from the self-assembly of Ubx proteins, fusion proteins comprising a Ubx protein, or fragments thereof.

In all embodiments, the ligands in the matrix are present on the solid support. Non-limiting examples of solid supports include activated alumina, powdered cellulose, silicic acid, gel, paper, glass fiber, plastic, agarose, sepharose, silica and derivatives thereof, and any other suitable solid support.

It was unexpectedly found that the binding capacity of the ligand is increased about 1,000 fold when the ligand is supported by Ubx materials. The binding capacity can be further increased by adding repeats of the ligand, through gene fusion, to Ubx materials, i.e., by creating fusion proteins containing Ubx and one or more repeats of the ligand. For example, and not to be limiting, the binding capacity can be increased by using a fusion protein comprising 18 SpA or Z domain repeats immobilized on Ubx materials (FIG. 3).

Figure 4:
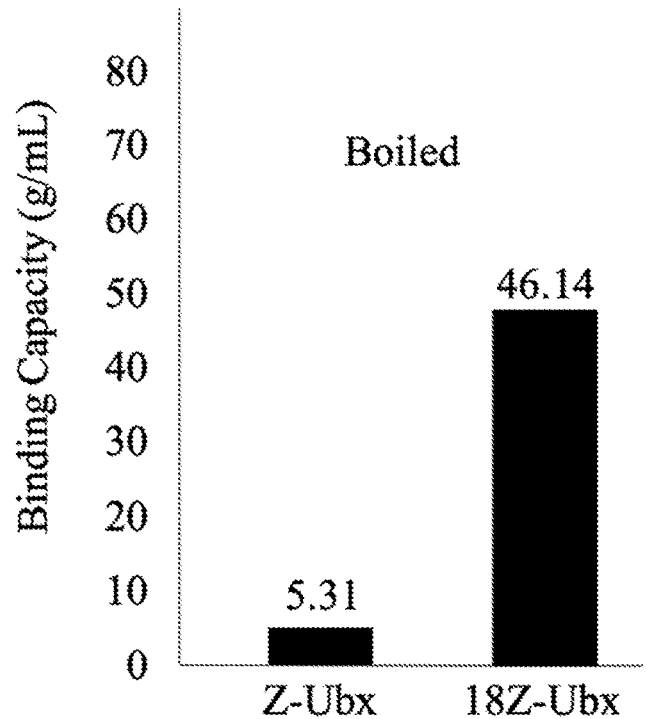
FIG. 4 is a graph showing quantification of static binding capacity for Z-Ubx and 18Z-Ubx after being submerged in boiling water for 30 seconds.

The compositions and methods provided herein can also be used to stabilize a ligand through covalent attachment to Ubx materials. In all embodiments, leaching or disassociation of the ligand from the solid support is prevented or reduced because the ligand is attached through protein fusion and produced in conjunction with the material forming the Ubx protein. As shown in FIG. 4, this stability is shown by the consistently higher binding capacity of the matrices described herein even after exposure to high heat (FIG. 4).

Also provided are methods of isolating an immunoglobulin such as IgG, IgA and/or IgM, wherein a ligand or a matrix according to the invention is used. Thus, the invention encompasses a process of chromatography, wherein at least one target compound is separated from a liquid by adsorption to a ligand or matrix described above. Thus, this aspect of the invention relates to affinity chromatography, which is a widely used and well-known separation technique. In brief, in a first step, a solution comprising the target compounds, preferably antibodies as mentioned above, is passed over a separation matrix under conditions allowing adsorption of the target compound to ligands present on said matrix. Such conditions are controlled, e.g., by pH and/or salt concentration (i.e. ionic strength in the solution). Care should be taken not to exceed the capacity of the matrix, i.e. the flow should be sufficiently slow to allow a satisfactory adsorption and not damage the matrix. In this step, other components of the solution will pass through in principle unimpeded. Optionally, the matrix is then washed, e.g. with an aqueous solution, in order to remove retained and/or loosely bound substances. The present matrix is optionally used with an intermediate washing step utilizing additives such as solvents, salts or detergents or a mixture thereof. In a next step, a second solution, an eluent, is passed over the matrix under conditions that provide desorption, i.e. release of the target compound. Such conditions are commonly provided by a change of the pH, the salt concentration i.e. ionic strength, hydrophobicity etc. Various elution schemes are known, such as gradient elution and step-wise elution. Elution can also be provided by a second solution comprising a competitive substance, which will replace the desired antibody on the matrix.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to one or more molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Antibody Binding Test

A test of the functionality of Z domains fused to Ubx materials was conducted. Plain Ubx, Z-Ubx, and 18Z-Ubx fibers were assembled and placed in a 4-well plate. Each fiber was incubated in 250 µl of phosphate buffered saline (PBS) with anti-myelin basic protein human antibody (Abcam, Cambridge, UK; 1:300). The fiber was rinsed three times with phosphate buffered saline (PBS) and then detected using goat anti-human IgG labeled with fluorescein isothiocyanate (FITC) (Abcam). Because di-tyrosine bonds also fluoresce blue, plain fibers appear blue under 4',6-diamidino-2-phenylindole (DAPI) fluorescence. Images were captured using DAPI and FITC settings on the Nikon Eclipse Ti A1R inverted confocal microscope and analyzed using Nikon Elements Imaging Software. FIG. 2A shows that plain Ubx material fails to bind antibody; However, both Z-Ubx and 18Z-Ubx bind significant amounts of FITC labeled antibody. This initial test demonstrates that antibody can be bound specifically by Z domains fused to Ubx material and not by the material itself.

Binding Capacity

Static binding capacity of Z-Ubx and 18Z-Ubx were determined by incubating Z-Ubx and 18Z-Ubx fibers with purified IgG (1 mg/mL) for 15 minutes. Fibers were rinsed three times in PBS before elution in 100 µl of 2.5 M Potassium Iodide pH 7. Eluent was run on an 8% SDS-PAGE acrylamide gel. Binding capacity was measured using densitometry analysis conducted with NIH Image J image analysis software. FIG. 3 shows that Z-Ubx fibers have a static binding capacity of 7.43 g/mL while 18Z-Ubx fibers have a static binding capacity of 67.86 g/mL.

Durability

Figure 5:
FIG. 5 shows a first and second purification of IgG. Fractions from the purification of IgG by ZZ-Ubx membrane PBS washes (lane2 and 5), load (lane 3), flow through (lane 4), and elution (lanes 6 to 10) were run on a 10% SDS-PAGE gel with the molecular weight marker in lane 1.
Figure 5:
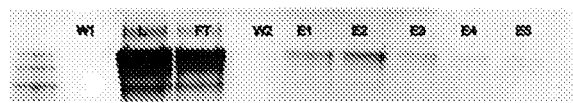
Figure 6:
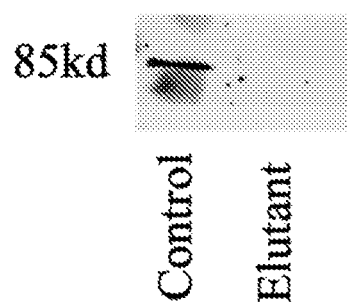
FIG. 6 is a Western blot of Z-Z-Ubx control (lane 1) and elution (lane 2). Primary is a rabbit anti-Protein A Z domain (1:150). Secondary is a goat anti-rabbit HRP conjugate (1:20000).

To examine durability of both Ubx materials and the stability of Z domains fused to Ubx materials, the same experiment was conducted; however, fibers were boiled in water for 30 seconds and allowed to cool at room temperature for one minute prior to binding purified IgG. After boiling, Z-Ubx fibers have a static binding capacity of 5.35 g/mL while 18Z-Ubx fibers have a static binding capacity of 46.14 g/mL (FIG. 4). This demonstrates that while some binding is lost, immobilization of Z domain on Ubx materials retains function even after exposure to extreme heat. To further test whether the low pH buffer affects the Z-Z-Ubx materials, the purification of IgG was run twice using the same membrane. Z-Z-Ubx membranes were washed with 10 ml of PBS at a flow rate of 0.5 ml/min. The membrane was loaded with monoclonal IgG at a flow rate of 0.5 ml/min and the flow through was collected. The membrane was extensively washed with PBS at a flow rate of 0.5 ml/min. The bound IgG was eluted with 0.1 M glycine pH 2.5 at a flow rate of 0.5 ml/min and fractions taken. The membrane was extensively washed with PBS and the IgG was loaded onto the membrane again as described. Fractions were run on an SDS-PAGE gel (FIG. 5). Two observations can be made from these gels: (1) the binding of IgG to the membrane on the second run is as good if not better than the first run, (2) Z-Z-Ubx oligomers are not observed in the wash steps, lanes 2 and 5, of either run. These observations suggest the low pH of the elution buffer does not affect the binding capacity of the Z-Z-Ubx nor does it cause leaching of the materials. Additionally, Z-Z-Ubx membranes were subjected to an additional 50 mL wash of elution buffer before a fraction was collected and run on a 10% SDS-PAGE gel next to purified Z-Z-Ubx monomer as a control. The gel was transferred onto a nitrocellulose membrane for Western blot analysis. The nitrocellulose membrane was blocked with 5% milk. To confirm that no leaching occurred, an anti-Z domain antibody was used to look for degradation and leeching from the membrane (FIG. 6). From these data it can be observed that Protein A ligand does not leach from membranes after treatment with a low pH buffer.

Purity and Activity

Figure 7:
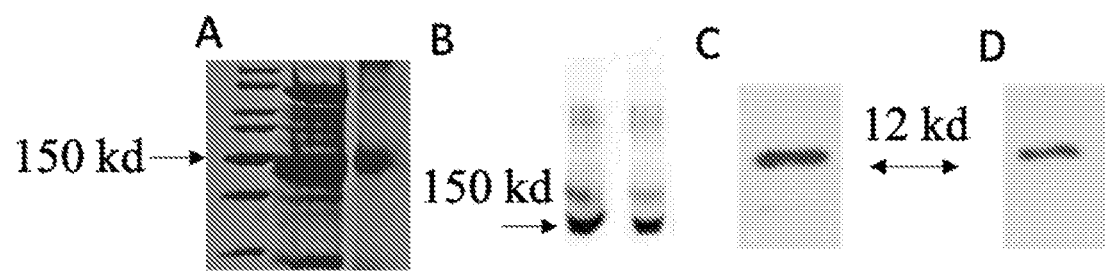
FIG. 7A is an SDS-PAGE gel showing antibody purification out of hybridoma media (lane 2) and eluted (lane 3).
FIG. 7B is a Western blot of IgG in hybridoma media (lane 1) and purified IgG (lane 2). Antibody is able to retain activity after purification over ZZ-Ubx membrane.
FIG. 7C shows that a pure, commercial antibody was used as a primary antibody to detect albumin in a Western blot. The secondary antibody is a goat Anti-Rabbit IgG (HRP).
FIG. 7D shows that an antibody purified from hybridoma media was used as a primary antibody to detect albumin in a Western blot. The secondary antibody is a goat Anti-Rabbit IgG (HRP).

The ability of Z-Z-Ubx membranes to purify monoclonal human Anti-Insulin antibody (Abcam) from hybridoma media was measured. Z-Z-Ubx membranes were washed with PBS at a flow rate of 0.5 ml/min. Hybridoma media spiked with Anti-Insulin antibody was then run over the membrane at 0.5 ml/min. The membrane was extensively washed with PBS before the elution of antibody with 0.1 M glycine pH 2.5. Fractions were collected from the start and elution 2 and run on a 10% SDS-PAGE gel (FIG. 7A). Fractions from the start and elution 2 were also transferred onto a nitrocellulose membrane for Western blot analysis. The nitrocellulose membrane was blocked with 5% milk. To confirm the presence of IgG (FIG. 7B) goat anti-human secondary was used. From these data it can be observed the antibody is >90% pure. Finally, the antibody retains activity. We compared the efficacy of untreated human Anti-Insulin antibody (Abcam) (FIG. 7C), to antibody purified using Z-Z-Ubx membrane (FIG. 7D) using Western blot analysis. Insulin was run on an 20% acrylamide gel and was transferred to a nitrocellulose membrane. The nitrocellulose membrane was blocked with 5% Milk. Insulin was detected with antibody not run over the membrane and antibody eluted from the Z-Z-Ubx membrane as a primary antibody. The goat anti-human secondary (abcam) was used to detect the primary antibody and the nitrocellulose membrane was imaged with Biorad Imager. The purified antibody demonstrates near wild type activity.

What is claimed is:

1. A Ubx biomaterial comprising two or more self-assembled fusion proteins, wherein each fusion protein comprises at least one Ubx protein and an immunoglobulin binding protein, wherein the immunoglobulin binding protein comprises one or more monomeric domains of domain Z or an immunoglobulin binding functional variant thereof, wherein domain Z comprises an amino acid sequence having at least 95% identity to SEQ ID NO: 1, and wherein the immunoglobulin binding protein is linked to the N-terminus of the Ubx protein via a linker.

2. The Ubx material of claim 1, wherein the immunoglobulin binding protein contains two or more monomeric domains of domain Z, wherein the monomeric domains are the same.

3. The Ubx biomaterial of claim 1, wherein the Ubx protein comprises SEQ ID NO: 20, and wherein the immunoglobulin binding protein comprises SEQ ID NO: 1.

4. A solid matrix comprising the Ubx biomaterial of claim 1.

5. The matrix of claim 4, wherein leaching of the immunoglobulin binding protein from the solid matrix is prevented or reduced.

6. The matrix of claim 4, wherein the binding capacity of 1 mL of Ubx material is greater than 1 g/mL.

7. A method for isolating an immunoglobulin from an immunoglobulin-containing solution comprising:

a) contacting the immunoglobulin-containing solution with the solid matrix of claim 4 under conditions wherein immunoglobulin contained in the solution is adsorbed to the matrix;

b) washing the adsorbed immunoglobulins; and c) eluting the immunoglobulin from the matrix.

8. The Ubx material of claim 1, wherein the Ubx protein and the immunoglobulin binding protein are linked via a linker comprising (SGSG)n (SEQ ID NO: 24) or (GSGS)n (SEQ ID NO: 25), wherein n is an integer.

9. The Ubx material of claim 8, wherein the immunoglobulin binding protein comprises about two or about 18 monomeric domains of domain Z, wherein domain Z comprises an amino acid sequence having at least 95% identity to SEQ ID NO: 1.

* * * * *